(12) United States Patent  
Tichauer

(10) Patent No.: US 10,401,374 B2  
(45) Date of Patent: Sep. 3, 2019

(54) DEVICE AND METHOD OF DETECTING AND GENERATING COMBINED MODULATED PARTICLE WAVE-FRONTS

(71) Applicant: Tichauer Technical Laboratories, LLC, La Palma, CA (US)

(72) Inventor: Larry M. Tichauer, La Palma, CA (US)

(73) Assignee: TICHAUER TECHNICAL LABORATORIES, LLC, La Palma, CA (US)

( * ) Notice: Subject to any disclaimer, the term of this patent is extended or adjusted under 35 U.S.C. 154(b) by 0 days.

(21) Appl. No.: 14/954,132

(22) Filed: Nov. 30, 2015

(65) Prior Publication Data

US 2016/0172155 A1 Jun. 16, 2016

Related U.S. Application Data

(60) Provisional application No. 62/085,591, filed on Nov. 30, 2014, provisional application No. 62/085,594, filed on Nov. 30, 2014, provisional application No. 62/085,597, filed on Nov. 30, 2014, provisional application No. 62/085,599, filed on Nov. 30, 2014.

(51) Int. Cl.
*G01N 37/00* (2006.01)
*G01N 22/04* (2006.01)

(52) U.S. Cl.
CPC ........... *G01N 37/005* (2013.01); *G01N 22/04* (2013.01)

(58) Field of Classification Search
CPC ......... G01T 7/00; G01N 37/005; G01N 22/04

USPC ................. 250/306, 307, 310, 311
See application file for complete search history.

(56) References Cited

U.S. PATENT DOCUMENTS

| | | | | |
|---|---|---|---|---|
| 5,602,820 | A * | 2/1997 | Wickramasinghe | G11B 5/00 250/216 |
| 6,038,018 | A * | 3/2000 | Yamazaki | H01J 37/28 356/237.1 |
| 6,310,341 | B1 * | 10/2001 | Todokoro | H01J 37/05 250/305 |
| 7,075,072 | B2 * | 7/2006 | Hatakeyama | G01N 21/9501 250/306 |
| 7,132,640 | B2 * | 11/2006 | Diaz | G01N 21/47 250/216 |
| 7,176,450 | B2 * | 2/2007 | Hollingsworth | G01Q 10/04 250/234 |
| 2009/0101817 | A1 * | 4/2009 | Ohshima | H01J 37/244 250/310 |
| 2010/0237252 | A1 * | 9/2010 | Jin | H01J 37/244 250/370.08 |

(Continued)

*Primary Examiner* — Michael Maskell  
(74) *Attorney, Agent, or Firm* — Fountainhead Law Group P.C.

(57) ABSTRACT

The present disclosure relates to a particle and energy detection system. More particularly, the present disclosure relates to coherent particle generation/detection devices configured to detect a plurality of particles (or energy quanta) which are caused to be combined by superposition upon impacting the detector and imparting a portion of their kinetic energy to the detection process. Additionally, a low power particle generating system that uses a particle generator device configured to generate a plurality of excitation signals which are caused to be focused and impinge upon a separating mechanism is provided so as to direct the particle beam to optimize the system's detection capability.

13 Claims, 19 Drawing Sheets

(56) References Cited

U.S. PATENT DOCUMENTS

| | | | |
|---|---|---|---|
| 2012/0235036 A1* | 9/2012 | Hatakeyama | G01N 23/2251 250/310 |
| 2013/0009058 A1* | 1/2013 | Tanaka | H01J 37/073 250/311 |
| 2013/0099116 A1* | 4/2013 | Stowe | H01J 37/244 250/310 |
| 2016/0148780 A1* | 5/2016 | Agrawal | H01J 37/244 250/307 |

* cited by examiner

DEVICE AND METHOD OF DETECTING AND GENERATING COMBINED MODULATED PARTICLE WAVE-FRONTS

RELATED APPLICATIONS

This patent application claims priority to and the benefit of U.S. Provisional Patent Application No. 62/085,591, filed Nov. 30, 2014, and entitled "Device and Method and Apparatus for Target Identification Using Tunneling Photon Effect using Crystalline Drivers," U.S. Provisional Patent Application No. 62/085,594, filed Nov. 30, 2014, and entitled "Device and Method of Producing Combined Acoustic Modulated Wave-fronts," U.S. Provisional Patent Application No. 62/085,597, filed Nov. 30, 2014, and entitled "Device Apparatus and Method of Generating Pulsed Particle Beams," and U.S. Provisional Patent Application No. 62/085,599, filed Nov. 30, 2014, and entitled "Device and Method of Detecting Combined Acoustic Modulated Wave-fronts," the contents of each of which are incorporated herein by reference.

FIELD OF THE DISCLOSURE

The present disclosure generally relates to a system and method for detecting particles and energy.

BACKGROUND

Various types of sensors and sensing systems are used in a wide range of contexts to determine characteristics of objects and environments. Often, sensors are designed to detect one type of particle or energy. As a simple example, photodetectors are used to detect light. More complex sensing systems are used to conduct materials analysis or to assist with medical diagnoses. For example, magnetic resonance imaging employs magnetic fields and radio waves to create images of a human or animal bodies.

However, current sensing techniques suffer from disadvantages. Sensors often must be implanted within a sample or subject, potentially destroying the sample (e.g., as in the case of destructive testing) or causing pain or discomfort for a subject. Further, current sensors are limited in their ability to detect particular types of particles and/or energy. Accordingly, there exists a need for new sensing techniques and systems for detecting particles and energy.

SUMMARY

In accordance with the presently claimed invention, a system and method for detecting particles and energy and energy is provided.

In accordance with one embodiment of the presently claimed invention, a sensor apparatus comprises: a processor coupled to a display; a power supply with a positive terminal and a negative terminal; a semiconductor with a p-type region and an n-type region, wherein the p-type region is coupled to the negative terminal and the n type region is coupled to the positive terminal via a load, thereby forming a reverse-biased P-N junction on the semiconductor; and a detector configured to measure the voltage across the load and generate a detected signal; wherein the processor is coupled to the detector and is configured to: amplify and filter the detected signal to create a measurement signal; and provide a display signal to the display that is representative of the measurement signal.

In accordance with an embodiment of the presently claimed invention, a system for generating excitation signals and receiving excited particles comprises: a particle generator configured to emit a plurality of excitation signals; a target which receives the plurality of excitation signals and emits a plurality of emitted particles; a particle receiver comprising a sensor and a beam focusing element, the beam focusing element comprising: a filter which blocks at least a first portion of the plurality of emitted particles and passes at least a second portion of the plurality of emitted particles; a focusing element which focuses the second portion of the plurality of emitted particles; and a refraction element which refracts the second portion of the plurality of emitted particles such that a plurality of desired particles impinge on the sensor; and a controller coupled to the sensor and configured to generate a measurement signal representative of the plurality of desired particles.

In accordance with one embodiment of the presently claimed invention, a method for detecting and identifying a characteristic of a sample is provided, the method comprising: directing a plurality of excitation signals at the sample; receiving, with a particle receiver comprising a sensor, a plurality of emitted particles emitted by the sample in response to the plurality of excitation signals, the plurality of emitted particles comprising a plurality of desired particles and a plurality of undesired particles; filtering the plurality of emitted particles such that the plurality of undesired particles is prevented from impinging on the sensor and the plurality of desired particles is directed towards the sensor; creating, with the particle receiver, a measurement signal indicative of the plurality of emitted particles received by the particle receiver; and determining, based on the measurement signal, the characteristic of the sample.

BRIEF DESCRIPTION OF THE DRAWINGS

The following disclosure as a whole may be best understood by reference to the provided detailed description when read in conjunction with the accompanying drawings, drawing descriptions, abstract, background, field of the disclosure, and associated headings. Identical reference numerals, when found on different figures, identify the same elements or functionally equivalent elements. The elements listed in the abstract are not referenced but nevertheless refer by association to the elements of the detailed description and associated disclosure.

DETAILED DESCRIPTION

Figure 1:
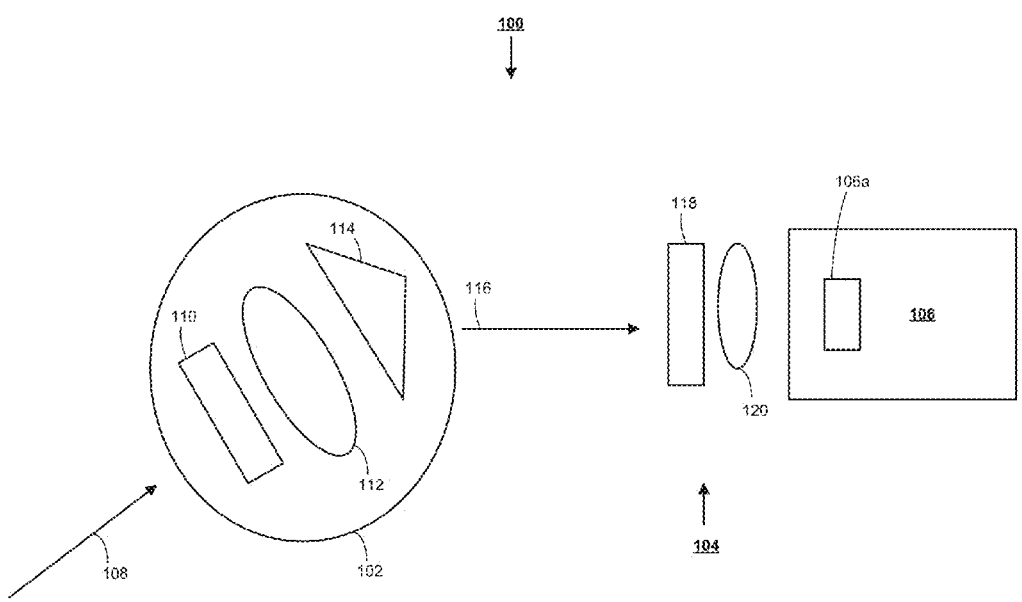
FIG. 1 is a steerable beam focusing device in accordance with an embodiment of the present disclosure.

The present disclosure is not limited to the particular details of the apparatus depicted, and other modifications and applications may be contemplated. Further changes may be made in the apparatus, device, or methods without departing from the true spirit and scope of the disclosure herein involved. It is intended, therefore, that the subject matter in this disclosure should be interpreted as illustrative, not in a limiting sense.

The present disclosure provides a particle detection system that uses a single detection device or an array of coherent particle detection devices (referred to herein as a "detection device") configured to detect a plurality of particles. In an embodiment, the detection device comprises a particle receiver and is configured to detect particles as the particles impart a portion of their kinetic energy to the particle receiver (e.g., in the form of electric current. In an embodiment, the current generated by a plurality of particles impinging on the detection device is combined. In various embodiments, the detection device comprises one or more of: a kinetic energy detector (such as a photomultiplier), a photo detector, a seismic detector, a reverse-biased semiconductor junction, and a piezoelectric sensor. In an embodiment, the particle receiver is supercooled (e.g., through the use of a supercooled cooling liquid). In an embodiment, portions of the detection device are configured to rotate and pivot so as to displace and direct at least a portion of a beam of particles or excitation signals to the particle receiver. In an embodiment, the detection device comprises a combination of one or more of the group comprising a focusing element, a filtering element, and a separating element which are configured to filter and direct desired particles to the particle receiver while preventing the particle receiver from intercepting undesired particles.

In an embodiment, a low power particle generating system comprising a particle generator device configured to generate a plurality of excitation signals is used to assist in directing a particle beam to the particle receiver, thereby optimizing the system's detection capability. In an embodiment, a focusing element is used to focus the excitation signals on a desired target. In an embodiment, the focusing system comprises an optical lens comprising one or more of a highly crystalline structure, a homogeneous structure, or a compound structure. In an embodiment, the particle generating system comprises a separating mechanism comprising a plurality of separators such as prisms and/or other structures having multiple facets to facilitate the angular displacement of the plurality of excitation signals produced by the particle generator. In an embodiment, the particle generating system comprises a rotating and pivoting portion configured to displace and direct at least a portion of the excitation signals produced by the particle generator towards a target. In an embodiment, the rotating and pivoting portion comprises a separator configured to filter and separate the particle mix before the mix is discharged and intercepted by a sensor or detector positioned externally with respect to the position of the particle generator. In an embodiment, the separated particle fluxes are individually detected and demodulated.

FIG. 1 depicts an embodiment of a beam focusing device 100 used with a detection device. As shown, the beam focusing device 100 comprises a first stage 102, a second stage 104, and a particle receiver 106. In an embodiment, the particle receiver 106 senses particles by detecting energy indicative of the particle's presence. An incident beam 108 of particles, comprising both particles to be detected (desired particles) and extraneous particles (undesired particles), is intercepted by the first stage 102. The first stage 102 comprises a filter 110, a focusing element 112, and a refraction element 114. The filter 110 blocks at least a portion of the undesired particles, while permitting desired particles to pass. The focusing element 112 focuses the desired particles, which are refracted by the refraction element 114. In an embodiment, the first stage 102 separates particles in the incident beam 108 according to one or more of their composition, energy level, and excitation level.

In an embodiment, the first stage 102 is configured to rotate and pivot with respect to the remainder of the focusing device 100. The first stage 102 is configured to both rotate and move tangentially with respect to the direction of rotation.

The resultant beam 116 exits the first stage 102. In an embodiment, the resultant beam 116 is directed to the second stage 104 comprising an additional filter 118 configured to further reduce the amount of extraneous particles which could excite the particle receiver 106. In an embodiment, the second stage 104 comprises an additional focusing element 120, which allows for additional particle concentration prior to the particles impinging on the particle receiver 106. The particle receiver 106 is configured to receive a mix of particles. In an embodiment, the type of particles received is determined by the generating source. In an embodiment, the particle receiver 106 is configured such that the higher the energy/cm$^2$ is, the greater the effective sensitivity of the particle receiver will be (e.g., the signal to noise ratio is increased). In an embodiment, the ratio of the energy level to the particle mix is proportional to the energy of the incident particles after selective filtering as well as the attendant filtering losses. The construction and material for the beam focusing device 100 (e.g., the components comprising the first stage 102 and/or the second stage 104) are selected based on their ability to separate and select certain desired particles for reception and simultaneously redirect other undesired particles. In an embodiment, the configuration of the beam focusing device 100 is determined so as to preferentially accentuate one particle's response relative to others. This may be accomplished, for example, by varying the distance between, as well as the material selection of, the components of the beam focusing device 100.

In an embodiment, an optimized configuration of the beam focusing device 100 allows for maximizing the receiver sensitivity. For example, in an embodiment where the beam is used to carry information (e.g., the beam is used in a communication device), maximizing the receiver sensitivity increases the potential for higher available information bandwidth. In a related embodiment, the realized information throughput is reduced by added channel overhead so as to compensate for any signal to noise ratio corrections required for the end-to-end system, thereby minimizing errors in information/energy transfer.

Figure 2:
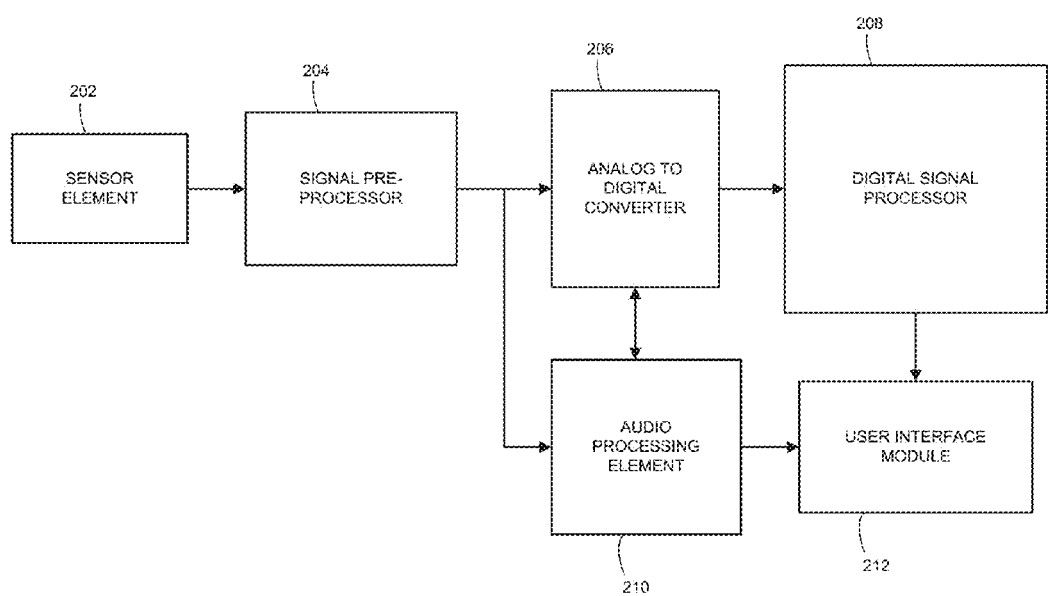
FIG. 2 is a block diagram of a particle receiver in accordance with an embodiment of the present disclosure.

FIG. 2 depicts a block diagram of an embodiment of the elements comprising the particle receiver 106. As shown in FIG. 2, in an embodiment, the particle receiver 106 is a hybrid analog/digital particle receptor comprising a sensor element 202, a signal preprocessor 204, an analog-to-digital converter (ADC) 206, a digital signal processor (DSP) 208, an audio processing element 210, and a user interface module 212. The sensor element 202 produces a detected signal (also referred to as a measured signal) based on measurements indicative of desired particles, which is first processed by the signal preprocessor 204 before being converted to a digital signal by the ADC 206 and further processed by the DSP 208.

In an alternative embodiment, the detection device 100 is a purely analog detector and does not include any digital circuitry, thereby changing the particle sensing topology from that depicted in FIG. 2.

In a preferred embodiment, the sensor element 202 is supercooled. In an embodiment, the sensor element 202 is supercooled to a temperature of 20 milli-degrees Kelvin or lower such that the atoms within the sensor element 202 move as little as possible. In this manner, the sensitivity of the sensor element 202 is increased such that any energy impinging on the sensor element 202 (e.g., from a desired particle) will cause a sudden detectable signal that will result in an output from the sensor. In an embodiment, all of the elements preceding as well as following the sensor element 202 (including the design of the housing for the sensor element 202 itself) are configured to decrease the probability of an undesired detection event occurring by, for example, filtering the incoming energy such that only the desired wave-front species will be detected by the sensor element 202 itself. In an embodiment, any system elements following the sensor element 202 is tested for both resistance to the effects of the impinging energy as well as for their response to it so as to ensure that the potential system element's effect on system performance is acceptable.

In an embodiment, the sensor element 202 detects the impact of a particle striking it and imparting at least a portion of its energy to the sensor element 202 for purposes of detection. As will be understood by one of skill in the art, energy may be detected using piezoelectric devices and photonic detectors.

As shown in FIG. 2, in an embodiment, the particle receiver 106 is a hybrid analog/digital particle receptor capable of detecting the imparted energy from the particles which strike it. These particles may be subatomic in nature or may simply be described as energy quanta. These quanta can be ascribed a given kinetic energy based on the equation $E_n = 0.5 * m_n * v_n^2$, where $m_n$ is the imputed mass of the quanta and $v_n$ is the quanta's imputed velocity. The quanta's imputed velocity is used to compute the energy present within the quanta just prior to its impact with the sensor element 202. The detectable energy is equivalent to $E_{det} = (E_n - E_{n'}) + E_q$, where $E_{det}$ is the net detected energy, $E_{n'}$ is the energy remaining within the quanta after striking the sensor element 202, and $E_q$ is the quiescent noise energy within the sensor element 202. As will be clear to one of skill in the art based on this disclosure, it is highly desirable for the quiescent energy component of the sensor element 202 to be as close to zero as is possible, such that the ratio of imparted energy to quiescent energy is maximized. This results in maximum sensitivity. In an embodiment, this is achieved by bringing the quiescent temperature of the sensor element 202 as close to zero degrees Kelvin (that is, absolute zero) as possible. As will be clear to one of skill in the art, any sensor element capable of absorbing at least a portion of the incident energy may be used with the sensor element 202. The degree of sensitivity will also depend on the atomic structure of the sensor element 202. In an embodiment, a crystalline device with a homogeneous lattice structure is used; this structure results in a linear transducer as it suffers little mismatch in structure and therefore reacts essentially uniformly to a given quanta of energy regardless of the location at which the quanta impacts the sensor element 202.

In an embodiment, the signal preprocessor 204 filters and amplifies the measured signal detected by the sensor element 202. In embodiments, the sensor element 202 is configured to be either differential or single ended in nature. In an embodiment, the sensor element 202 is used as an element in an active feedback loop. As will be clear to one of skill in the art, any common mode signals which may be extraneously coupled to the sensor element 202, as well as any supporting bias circuitry or parasitic coupling paths, may be reduced or eliminated from the detection process early on. In an embodiment, the signal preprocessor 204 band limits the detected signal to a finite bandwidth so as to further minimize the amount of system noise. In this way, the amount of undesired signal spectral components presented to the analog-to-digital converter 206 are minimized. In a preferred embodiment, only the desired signal spectral components are presented to the ADC 206 and digitized. The number of bits of resolution in the digitized signal is determined by the dynamic range of the expected signal to be detected.

In an embodiment, the digital signal processor 208 further operates on the detected signal which has been digitized by the ADC 206. In an embodiment, the DSP 208 is configured to further filter as well as selectively amplify the detected signal using an algorithm specified by the particular application. In an embodiment, the operating algorithm is automatically selected by the DSP 208 based on the detected signal's characteristic. In an embodiment, the algorithm is user-selectable. In an embodiment, the detected signal is normalized. In an embodiment, the detected signal is enhanced by varying the denominator of the normalization equation, e.g., by using the equation: normalizedLevel= (measuredLevel−minimumLevel)/(maximumLevel−minimumLevel). In an embodiment, the first and/or second derivatives are used. In an embodiment, the frequency domain representation of the signal is used. As such, the scalar representation of the resultant detected signal may be magnified. In embodiments, the algorithm may use the first or second derivative of the signal. In an embodiment, the frequency domain representation of the signal is used as a "fingerprint" to characterize a sample under test.

In an embodiment, a user may identify the maximum level (maximumLevel) as well as the minimum level (minimum- Level), either in real time or in advance. In an embodiment, this function is accomplished automatically by the DSP 208. By properly choosing the values for maximumLevel and minimumLevel, the sensitivity may be multiplied as the difference between the maximum and minimum levels is smaller than the inherent dynamic range of the measurement system.

In an embodiment, the DSP 208 is configured to vary the characteristics of the sensor element 202, including but not limited to gain, phase, frequency response, or any combination thereof. In an embodiment, the DSP 208 is configured to receive external direction from a distributed and/or common system processor. In an embodiment, the DSP 208 varies the characteristics of the sensor element 202 based on one or more of the following: time, temperature, frequency distribution of the detected signal, and external direction received by the DSP 208.

In an embodiment, the audio processing element 210 is configured to provide an aural representation of the detected signal. The audio processing element 210 may receive the detected signal in either analog or digital form. In an embodiment, the audio processing element 210 is conditioned by either the DSP 208 or the user interface module 212.

In an embodiment, the detection device 100 includes a user interface module 212 configured to provide output to a user and/or receive input from a user. In an embodiment, the user interface module 210 comprises a processor connected to a storage device containing computer-readable instructions for generating a user interface. In an embodiment, the user interface module 210 comprises one or more output devices (e.g., a display, a speaker, a tactile feedback device, a light, etc.) and/or one or more input devices (e.g., a button, microphone, camera, light sensor, etc.). As will be clear to one of skill in the art based on this disclosure, the user interface may be either a digital or analog interface comprising a visual, aural, or tactile feedback mechanism to let the user or the detection system 100 (of which the particle receiver 106 is a part) know whether or not the energy detected is within certain desired parameters. The optimum representation to characterize the sample under test may be determined using any of the algorithms disclosed herein. In an embodiment, the user interface is configured to generate the optimum representation based on the output of the DSP 208. In an embodiment, the user interface module 212 generates a visual representation reflecting an array of particle receptors which, when their outputs are integrated, depict a visual image which represents the perceived state of the environment being sensed. In an embodiment, the user interface module 212 is configured to enable the user to declare certain measured characteristics to be modifiable both during or after a measurement is made. By way of example, but not limitation, the user interface module 212 may be configured such that a user may declare the maximum and minimum signal levels to be used to normalize the measured signal.

Figure 3:
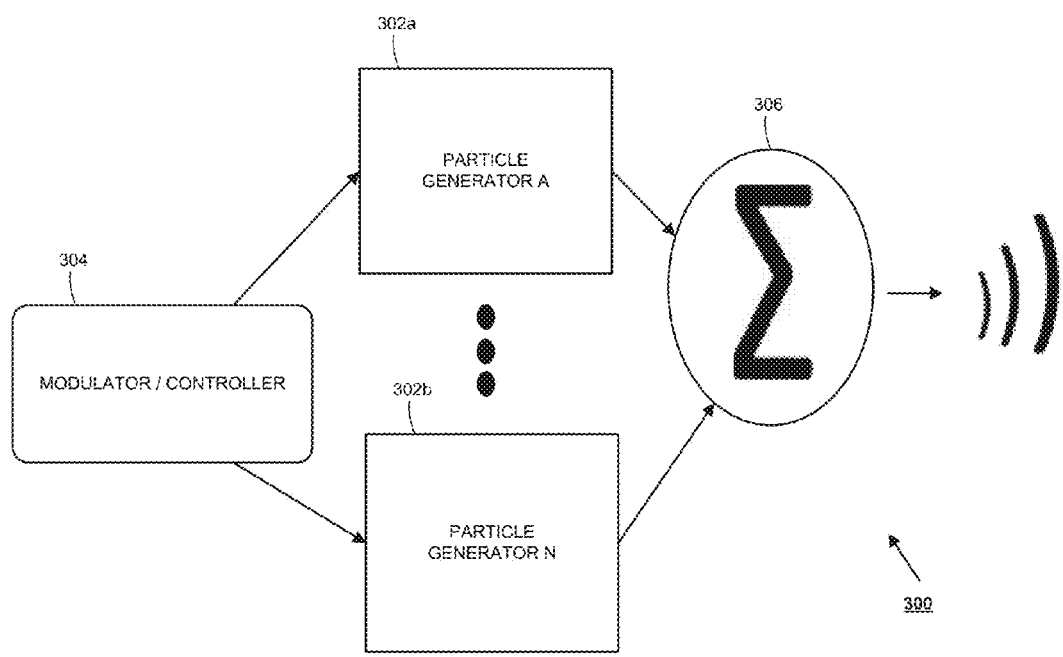
FIG. 3 is a particle generating system in accordance with an embodiment of the present disclosure.

FIG. 3 depicts an embodiment of a particle generating system 300. As shown, in an embodiment, the particle generating system 300 includes one or more particle generators 302 which are controlled by a controller 304. In embodiments with two or more particle generators 302 (e.g., particle generators 302a and 302b), the output from the particle generators 302 is combined together into a coherent wavefront 308. The controller 304 provides a modulating stimulus to each of the particle generators 302 as well as a synchronization stimulus that allows for proper phasing of the particle generators 302 with respect to each other, such that a desired coherent wave-front 308 will result.

In an embodiment comprising two or more particle generators 302, the resultant outputs of the two or more particle generators are coherently combined by a summing network 306. In an embodiment, the summing network 306 is a physical embodiment comprising one or more of a lens, one or more specialized materials, or a desired point in three dimensional space where the properly phased particle generator 302 outputs coherently combine resulting in a coherent wave front 308.

In an embodiment, individual wave fronts are combined by superposition. The electrical analog for this process is a current summing junction where in phase currents combine such that the resultant current flow exists as a linear summation of its constituent currents. In this embodiment, the wave front could be considered as a collection of particles whose collective energy could be quantified as energy per square unit of area as a function of time.

Figure 9:
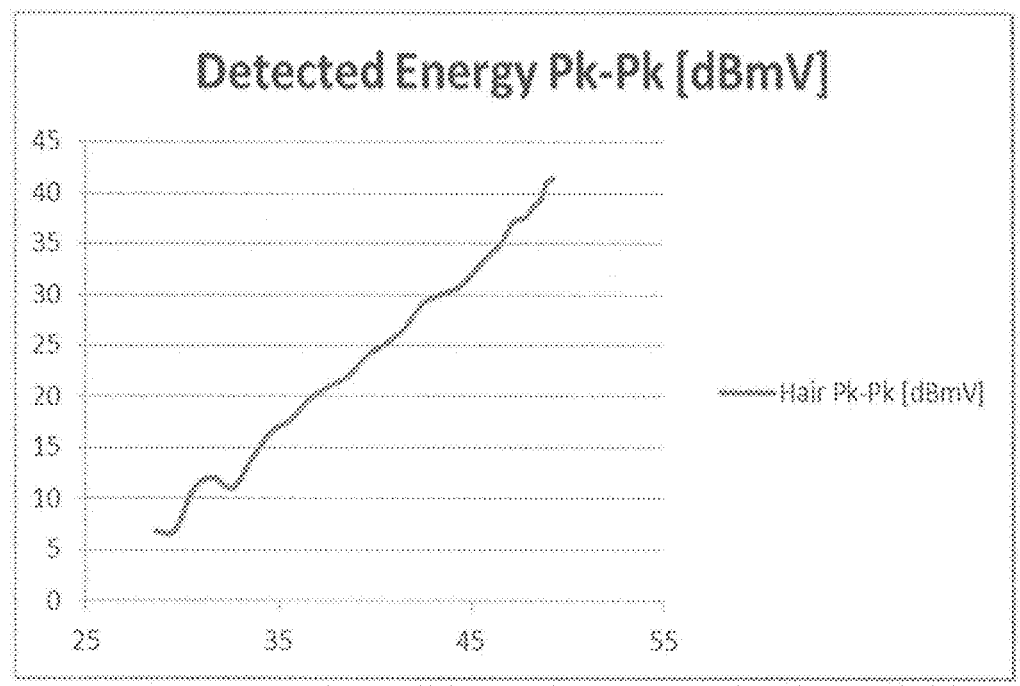
FIG. 9 depicts the peak-to-peak amplitude measured by a sensor in accordance with an embodiment of the present disclosure.

The modulation of the beams created by the particle generators 302 can include amplitude as well as phase modulation. As the particle mix is a function of power, as shown in FIG. 9, the particle mix can be modified by varying the peak power of the stimulating signal. In an embodiment, a synchronization signal is distributed to each particle generator 302 from the controller 304. In an embodiment, the synchronization signal is a function of time. In an alternative embodiment, the synchronization signal is a digital word which references a given system time, resulting in a desired coherent emission from a particular particle generator 302 (e.g., particle generator 302a). Each particle generator 302 may receive a different digital word, each configured to produce a specific desired coherent emission. In this way, the resultant instantaneous energy of the wave front 308 is configured to possess the desired characteristics as a function of time.

In embodiments, the particle generators 302 may be either co-located or spatially distributed. As will be clear to one of skill in the art from this disclosure, the formation of coherent wave fronts is desirable for various applications which using co-located or spatially distributed particle generators 302. As discussed further herein, this form of beam-steering may be used in a variety of applications, including material testing, communications systems, defensive systems, and offensive systems.

As will further be clear to one of skill in the art from this disclosure, the process of generating particle beams comprises multiple subprocesses, including the actual generation of the particles, condensing the particle flux, and containing the particle flux. Each of these subprocesses may be carried out by separate systems or components or by a single consolidated system. In an embodiment, the composition of the particle flux produced is dependent upon the amount of power and materials used in the raw generation process.

In an embodiment, a particle generator system comprises a coax-to-waveguide transition which is excited by a pulsed microwave signal fed into the coax port. The signal is then transmitted by an antenna element resident within the waveguide transition cavity to a waveguide horn antenna. The energy transmitted by the antenna element reacts with both the continuous and discontinuous portions of the waveguide, but reacts more strongly with the discontinuous portions. In an embodiment where a rectangular waveguide is used, the high-field points occur at the exterior corners of the waveguide and along the interior base of the radiating element; quanta are generated in these locations. A portion of the transmitted energy reacts with the walls of the waveguide because the high field points occur at these discontinuities. Aspects of this disclosure, including the foregoing embodiment, may be better understood by considering an extension of maser theory to a waveguide cavity. This is a new and novel approach. By way of example, the interaction between the energy and the walls of the waveguide is roughly analogous to the interactions which occur in a conventional maser. As is known to one of skill in the art, "[w]hen a maser material is pumped and then stimulated, the material will emit radiation. The emission is due to the downward transition of electrons from a higher level E2 to a lower level, E1." Dr. T. Koryu Ishii, *Maser and Laser Engineering*, pg. 29 (1980).

Figure 5:
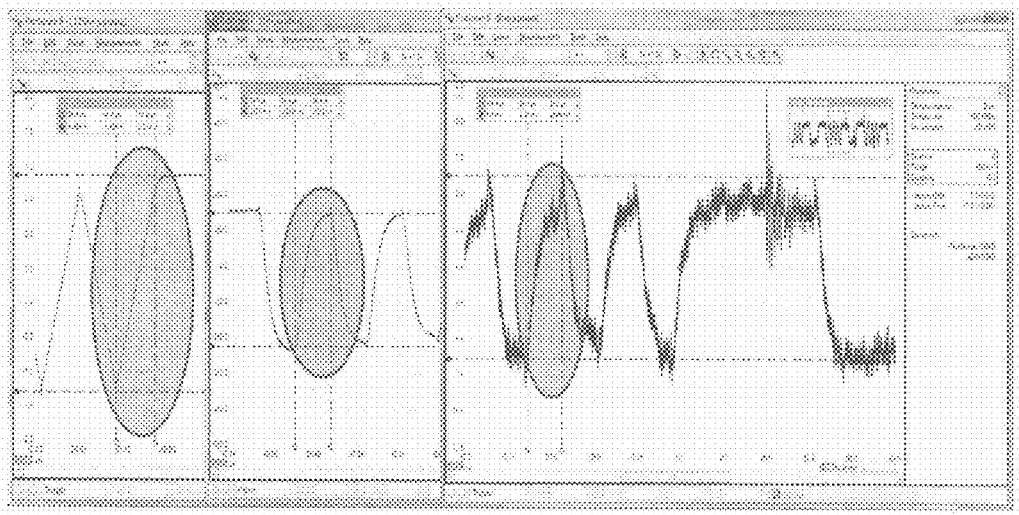
FIG. 5 is an exemplary embodiment of the changes in a particle mix as the particles proceed in a water channel in accordance with an embodiment of the present disclosure.

In an embodiment, high electric field concentrations occur in the corners of the waveguide rather than in the center of a conventional microwave horn antenna. In an embodiment, this effect is most noticeable at the rising and falling edges of the radio frequency (RF) envelope when a pulsed RF excitation is used. In alternative embodiments, other complex waveforms may be used. Further, other frequencies (aside from RF) may be used. In an embodiment, very high frequencies are used; the integrated energy of the envelope excites the observed effect and the individual cycles of the signal occur too rapidly as a function of time for the material to react. This effect is detected by a translational velocity effect that can be detected when delays can be measured in a water medium as shown in FIG. 5. In an embodiment, as the velocity decreases there is a corresponding increase in the mass associated with the energy. In an embodiment, applying the wave particle duality principle allows the energy (such as, but not limited to, RF energy) to be considered as a particle with a certain energy ascribed to it; the energy detected by the sensor can be considered a particle of much higher mass since the velocity has decreased to a very large degree from that of the speed of light.

Figure 4:
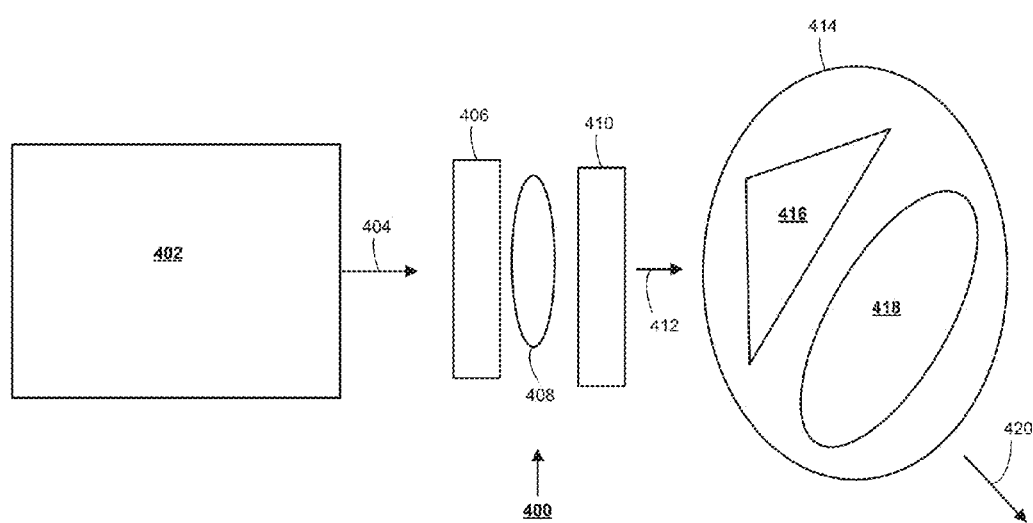
FIG. 4 is a particle generation and separation system in accordance with an embodiment of the present disclosure.

FIG. 4 depicts an embodiment of a particle generation and separation system 400 comprising a particle generator 402, an interface 406, a lens 408, a transition 410, and a movable assembly 414 comprising a refractor 416 and a filter 418.

In an embodiment, the particle generator 402 is configured to induce a plurality of excitation signals 404 to excite an interface 404. The interface 404 may comprise either a composite material or a single composition material. In an embodiment, excitation of the interface 404 results in the generation of a mixed particle signal species 412, which is focused by the lens 408 and aimed by the transition 410. The mixed particle signal species 412 is directed into the movable assembly 414, which is configured to rotate and pivot separately from the remainder of the particle generation system 400. The movable assembly 414 separates the incident particles according to energy and excitation levels using the refractor 416 and filter 418. In an embodiment, the movable assembly 414 is configured to pivot tangentially to its direction of rotation. The generator 400 can generate an array of particles based on the amount of power incident on the particle generating topology, as well as the mix of materials used to fabricate the system. The higher the energy/cm$^2$ is, the greater the particle mix will be. The energy level to particle mix ratio is dependent on the energy applied for particle generation. As will be clear to one of skill in the art, the construction of the particle generator 402 and the material selection for the interface 404 determines which particles are selected for transmission and allows other species that are generated at the same time by the particle generator 400 to be redirected away from the target. In other words, the combination of the particle generator 402 and the interface 404 may preferentially accentuate one particle's response relative to others. This is accomplished by varying the focal distance as well as the material selection of the components in the interface 404. In an embodiment, the particle generator comprises a waveguide transition. In an embodiment, a horn is attached to the waveguide transition. In an embodiment, the particle generator comprises a laser. In an embodiment, the particle generator comprises an LED.

Beam Modulation

The manner in which the system is applied or employed will determine the type of modulation used to excite particles using the particle generator 400. Similarly, the purpose of the system will determine the type of modulation used by the particle generator 400. The following enumerates characteristics of the beam that are adjusted (either alone or in combination) in various embodiments.

The beam's amplitude may be modulated, which allows for determining the types of particles generated by a given pulse.

The width of pulses may be modified, which allows for determination of the on time for a given pulse. For example, this is useful when attempting to pulse modulate a data stream as well as determining when and how much energy to direct to a given target over a period of time. In an embodiment, pulse width modulation is used when radiating cells in an organism, allowing for control over the amount and type of particles. In another embodiment, pulse width modulation is used in a closed loop system where a characteristic of the target is monitored in real time to determine if the dose, or mix, of particles needs to be modified.

In an embodiment, both amplitude modulation and pulse modulation are used simultaneously to optimize the characteristics of both features outlined above.

In an embodiment, a complex modulation scheme is used to allow not only for error correction and more efficient use of bandwidth but also allow multiple beams to exist simultaneously within the same bandwidth. This allows for multiple receivers to be matched to the emitted code, such that only the signal of interest is decoded and processed.

In an embodiment, the particle beam is directed so as to cause upsets in digital systems, similar to those commonly attributed to cosmic rays. By properly directing the beam, the probability of detection of any artifacts that the particle generator may emit in addition to the particulate matter is minimized. In an embodiment, the system is used to disable digitally based systems either terrestrially or extraterrestrially.

Sensor Design

FIG. 5 depicts an exemplary embodiment of the changes in the particle mix as the particles proceed in a water channel. The waveform composition changes and the rise time gets faster for each ensuing measurement. This may be due to the lower energy particles suffering larger attenuation than the higher energy particles, which may travel at a higher velocity. The sensor measures the summation of all the particles that impinge upon it as a function of distance in the aqueous medium. Since the higher energy particles will impart more energy to the sensor upon impact, they dominate in the frame capture to the far left and the rise time is seen to decrease as each frame is viewed from left to right.

Figure 6:
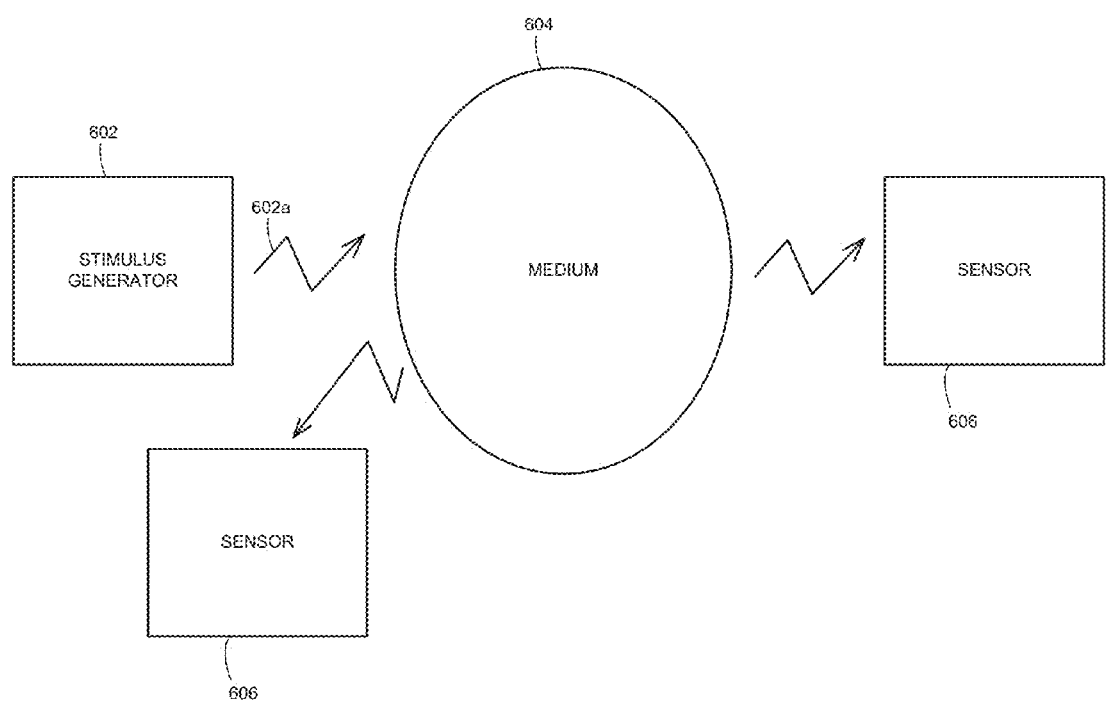
FIG. 6 is a block diagram of a detection system in accordance with an embodiment of the present disclosure.

FIG. 6 depicts a simplified block diagram of an embodiment of a detection system. Energy (e.g., energy quanta or particles) originates from a stimulus generator 602 (also referred to as a stimulus source or target). For example, in an embodiment, the stimulus generator 602 is a target which receives energy from a generating system 300. The energy travels through a medium 604 before reaching one of a plurality of sensors 606. The medium 604 could be solid, liquid, or vapor in nature. The medium 604 attenuates the energy and rejects a certain portion of the incident energy. The amount to which the energy is attenuated, reflected, and/or modified is dependent on the medium 604 (e.g., the composition of the medium 604)

Figure 7A:
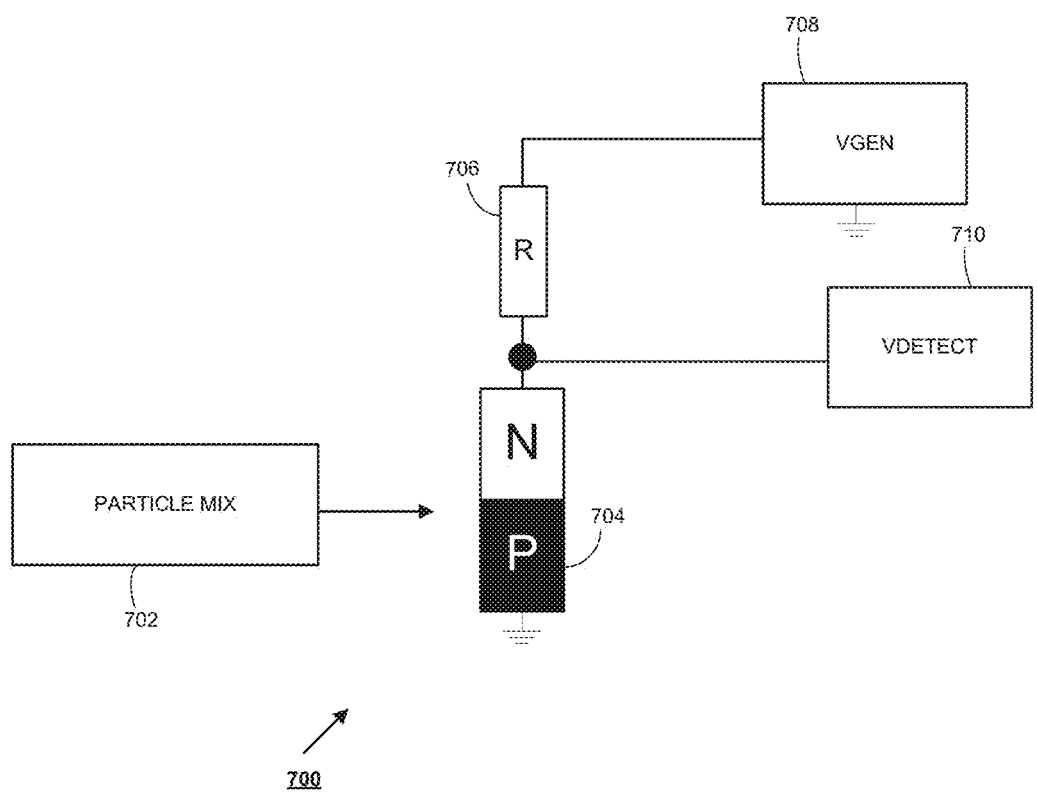
FIG. 7a is a diagram of a sensor in accordance with an embodiment of the present disclosure.

FIG. 7a depicts an embodiment of a sensor 700 used to detect a particle mix 702 (e.g., the energy quanta or particles depicted in FIG. 6). In an embodiment, the sensor 700 comprises a reverse-biased P-N junction 704, coupled to a voltage generator 708 via a resistor 706. A detected signal 710 may be measured between the P-N junction 704 and the resistor 706. In an embodiment, the resistor 706 is a variable resistor, with a resistance that may be changed as a function of time.

In an embodiment, the particle mix 702 impinges on the surface of the reverse-biased P-N junction 704. The reverse-biased P-N junction 704 detects the particle mix 700 as change in the capacitance across the junction, much like a photo detector detects impinging photons. However, while a photo detector may be used to detect the particle mix 700, not all implementations of a P-N junction are capable of detecting photons. For example, in an embodiment, the P-N junction 704 is housed in an opaque material (such as an epoxy) which precludes the detection of photons but not the detection of the particle mix 702.

As will be clear to one of skill in the art, other devices or structures besides reverse-biased P-N junctions may be used to detect energy quanta in accordance with this disclosure. In embodiments, one or more of the following devices are used in place of or in conjunction with the reverse-biased P-N junction: a photo transistor, a photo Darlington transistor, and a reverse-biased photo diode. In an embodiment, a phototransistor is used as a biasing element for the P-N junction.

In an embodiment, one or more op amps are used to boost the gain of the signal output by the sensor. In an embodiment, a two stage op amp design is employed for frequency domain measurements and a three stage op amp design is employed for time domain measurements.

In an embodiment, the sensor is placed on a printed circuit board. In various embodiments, the sensor placement is placed on the edge of the board, flat on a surface of the printed circuit board, or separated from the board (e.g., suspended in the air and connected to the board only by its leads). The particular configuration of the sensor may be selected depending on how the sensor will be swept across the sample under test. With a flat sensor, there is less opportunity for the sensor to be off axis and produce a biased measurement. In an embodiment, the sensor is placed tangentially to the sample under test so as to optimize the repeatability of the measurement. Edge-placed sensors allow for a narrow width sensor implementation. In an embodiment, the sensor cross section is dependent upon the die size and/or device packaging for the particular device used.

In an embodiment, the sensor is used with three stages of amplification, all located on a single printed circuit board. In an embodiment, a stand-alone PC board comprises a sensor and two op amp gain stages for frequency domain operation. The sensor may be mounted on the edge or a surface of the PC board. In an embodiment, the sensor is mounted 90 degrees to the conventional orientation of a second board containing a single op amp stage. This allows for a smaller footprint form factor for the sensor package. The sensor can be mounted on the edge or on the bottom of the PC board.

In an embodiment, the sensor is located remotely from an op amp stage, which allows for versatility in packaging.

In an embodiment, separate power supplies are used for two separate sections of the board. In embodiments, the board is either cut in two pieces or used as a single PC board with separate power supplies. The bias for the third stage is isolated from the first two stages for increased system stability so as to avoid the possibility of oscillation due to the total system gain. The resultant gain and phase ultimately determine the stability as a function of interstage isolation. In an alternative embodiment, the separate PC boards use a single power supply.

Although this disclosure generally refers to the sensor 700 as including a P-N junction as a detecting element, this disclosure contemplates other embodiments using the other disclosed structures as detecting elements.

Figure 7B:
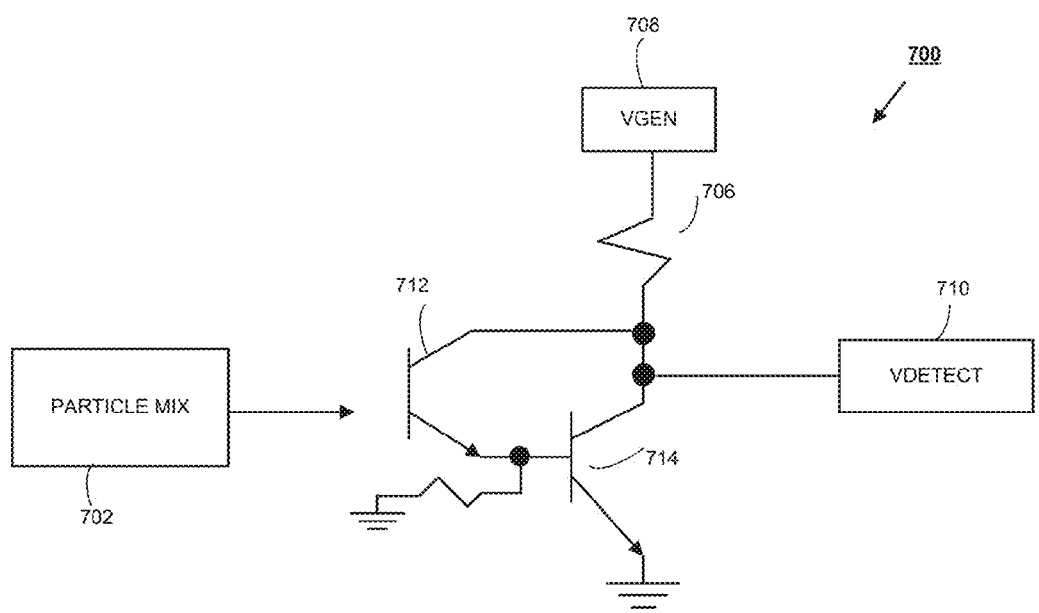
FIG. 7b is a diagram of a sensor in accordance with an embodiment of the present disclosure.

As shown in FIG. 7b, in an embodiment, a photo transistor 712 is used as part of a feedback loop and biases a transistor 714. The photo transistor 712 detects the particle mix 702, while the transistor 714 acts as a gain stage. In an embodiment, the photo transistor 712 is an infrared detector. In an embodiment, the transistor 712 is an NPN transistor. In a preferred embodiment, the transistor 712 is a 2N3094 transistor.

Figure 7C:
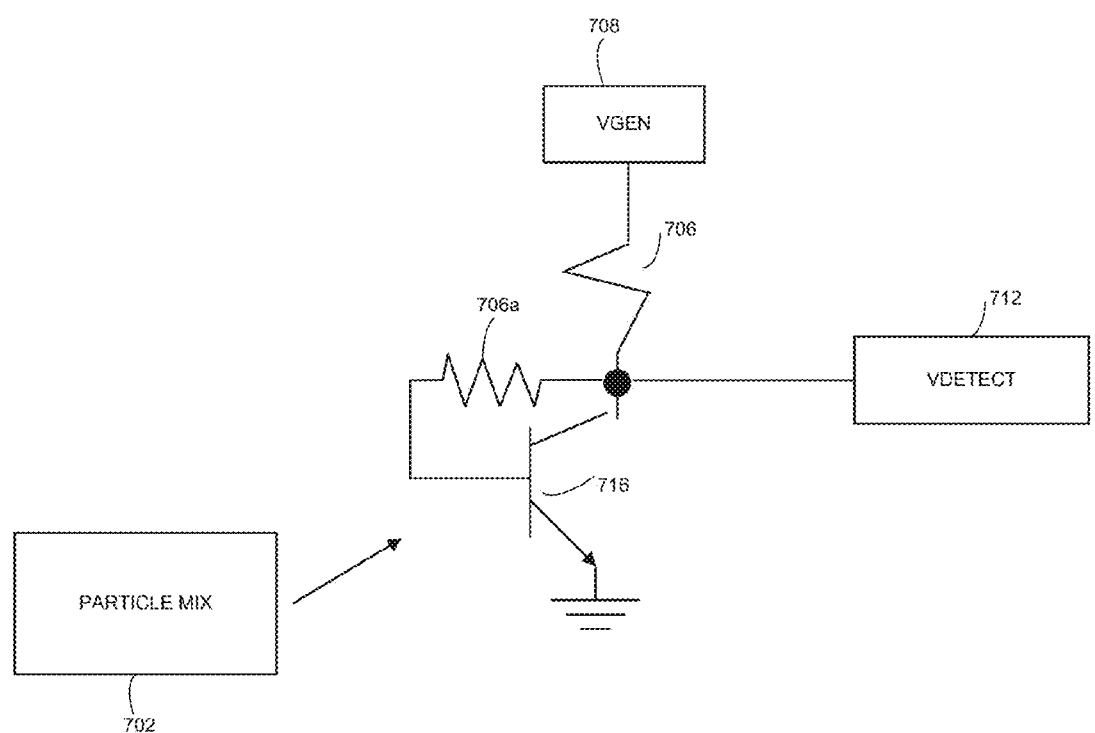
FIG. 7c is a diagram of a sensor in accordance with an embodiment of the present disclosure.

As shown in FIG. 7c, in an embodiment, a phototransistor 716 is used. In an embodiment, the phototransistor is an NTE3036 phototransistor. The sensor 700 may further comprise a biasing resistor 706a. In an embodiment, the biasing resistor 706a is a variable resistor. In an embodiment, the resistor 706 is a variable resistor. In an embodiment, the resistor 706 is a programmable current source. In an embodiment, automatic gain control (AGC) is performed using the resistor 706 (e.g., by changing the resistance of the resistor 706 or changing the current provided to the base of the transistor 716). In an embodiment, AGC is used to maintain a fixed quiescent output voltage for the transistor 716.

Figure 7D:
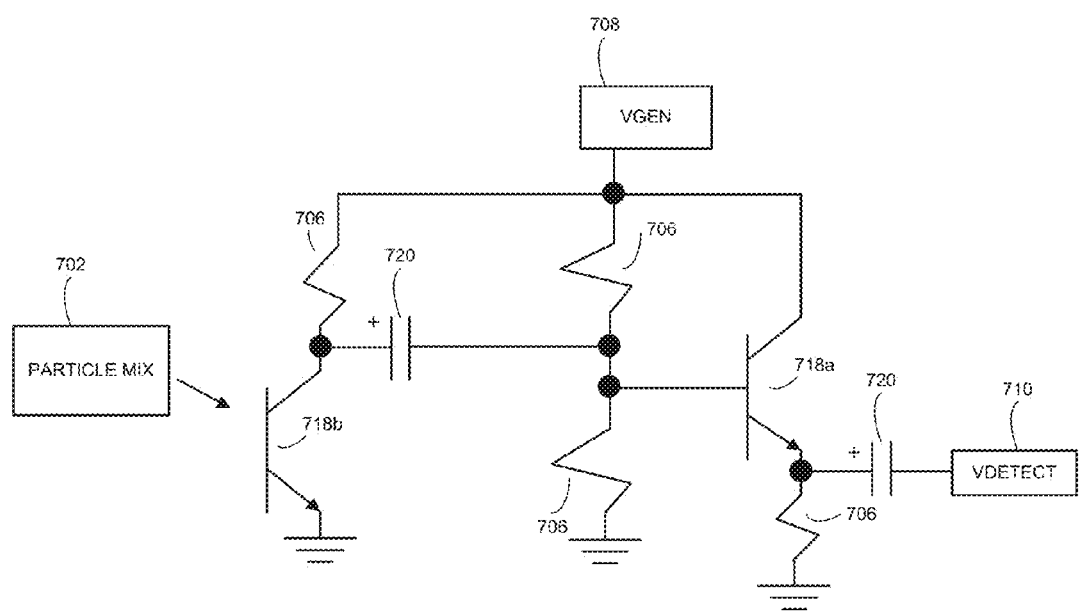
FIG. 7d is a diagram of a sensor in accordance with an embodiment of the present disclosure.

As shown in FIG. 7d, in an embodiment, a pair of transistors 718a and 718b are used. Transistor 718a is configured as an emitter follower. A plurality of resistors 706 and capacitors 720 may be used to configure the emitter follower. In an embodiment, the detecting transistor 718b is an SD5420-003 transistor. In an embodiment, the amplifying transistor 718a is an NPN transistor.

With reference to FIGS. 6 and 7a, the impinging particle mix 702 may contain more than one energetic species. The density of each impinging species is dependent on both the stimulus source 602, the medium 604, the characteristics of the P-N junction 702, the configuration of the sensors 606 as well as relative distances between all of the components. In embodiments, components of the detection system (e.g., the particular P-N junction 702, configuration of sensors 606, etc.) is selected so as to readily detect a particular impinging species.

In an embodiment, a plurality of P-N junctions may be arranged in an N×M array and configured such that N and M range anywhere from 1 element to many. Much like an array of photo diodes, the P-N junctions function to derive an image (e.g., each P-N junction corresponds to a pixel, creating an image). In an alternative embodiment, a single P-N junction 702 and/or the stimulus source 602 is moved, effectively creating a single pixel camera. In an embodiment, one or more P-N junctions are used to produce a 1, 2, 3, or 4 dimensional image where the 4th dimension is the spectral makeup of the detected signal.

This imputed 4th dimension may be better understood by considering the energy quanta generated by the stimulus source 602 to be particle-based, where the mass and velocity of each subcomponent of the particle mix can be quantified. The detection process is the translation of the combination of the mass and velocity of the impinging particles into a resulting current by the generated electron-hole pairs in the P-N junction, which are observed as the detected signal envelope (which can also be described by its Fourier components).

In an embodiment, sensor 602 comprises a processor configured to control the detection characteristics of the sensor 602 and/or the output characteristics of the sensor 602. As will be clear to one of skill in the art, in various embodiments, this process may be either digital or analog in nature and may provide an output in a variety of formats, including as either a scalar or a vector. In a preferred embodiment, the sensor 602 provides an output indicative of a relative strength describing the amplitude of the detected envelope as a function of time.

In an embodiment, the P-N junction 704 is the detecting element (i.e., the element which generates a signal indicative of the particle mix 702). As will be clear to one of skill in the art, the higher the gain of the transistor at low current, the better the response will be. For example, the lower the Fermi potential the easier it is to create an electron-hole pair. As will be further appreciated by one of skill in the art, higher frequency transistors have smaller depletion regions and thus may be preferable.

Technology Applicability

The detection system of the present disclosure is envisioned as having wide applicability.

Figure 8:
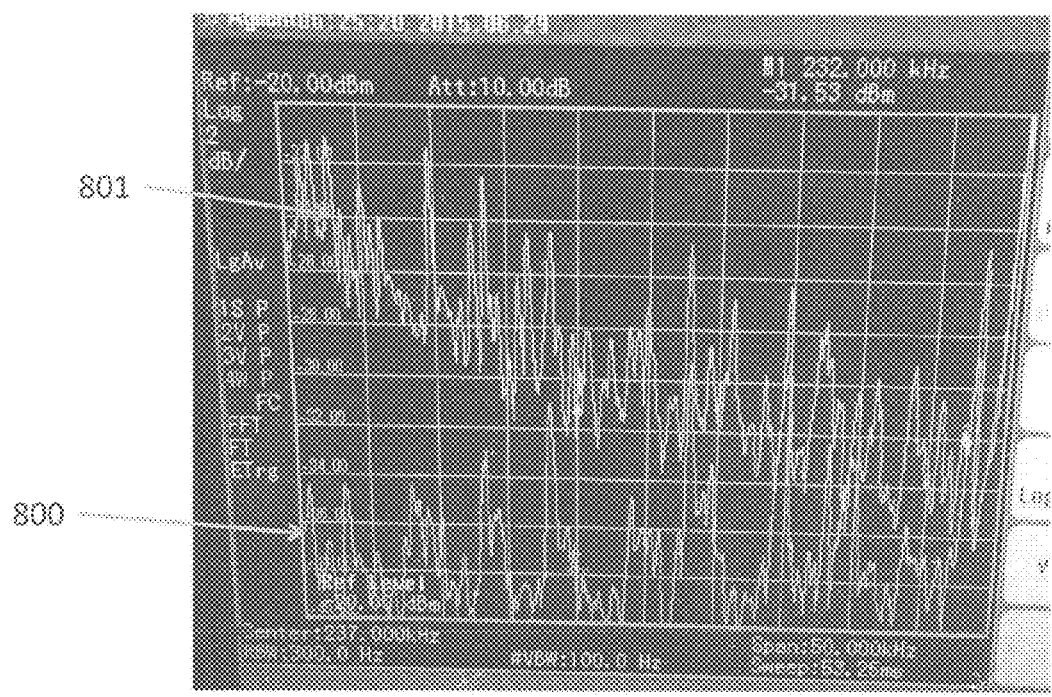
FIG. 8 depicts an exemplary spectral output measured by a sensor at two locations on a human body in accordance with an embodiment of the present disclosure.

In an embodiment, the detection system is used to locate acupuncture points measuring the particles detected at multiple locations on a human body. FIG. 8 depicts an exemplary spectral output measured by a sensor 700 at two locations on a human body: an acupuncture point 801 and the adjacent tissue 800. The relative energy levels detected at each point are shown as a function of frequency. In an embodiment, analysis of the amplitude modulated envelope of the detected signal enables detection of an acupuncture point by comparing the relative differential envelope amplitudes for spectral output. In an embodiment, the spectral output detected from a human body is used to differentiate and quantify/qualify various metabolic activities in the tissue itself. For example, by measuring the spectral output at a plurality of acupuncture points 801, the relative metabolic activity level of the tissue may be determined, which can provide an indication of the health of various portions of an individual's body. For example, increased metabolic activity near a wound may be indicative of an infection or other medical condition. This capability allows for the monitoring of synaptic activity as well as biologic and nonbiologic processes. In an embodiment, the detection system is used to locate and characterize cancerous tissue (as compared to benign tissue) due to variances in metabolic activity, which can be observed by both time domain as well as frequency domain representations.

Figure 16:
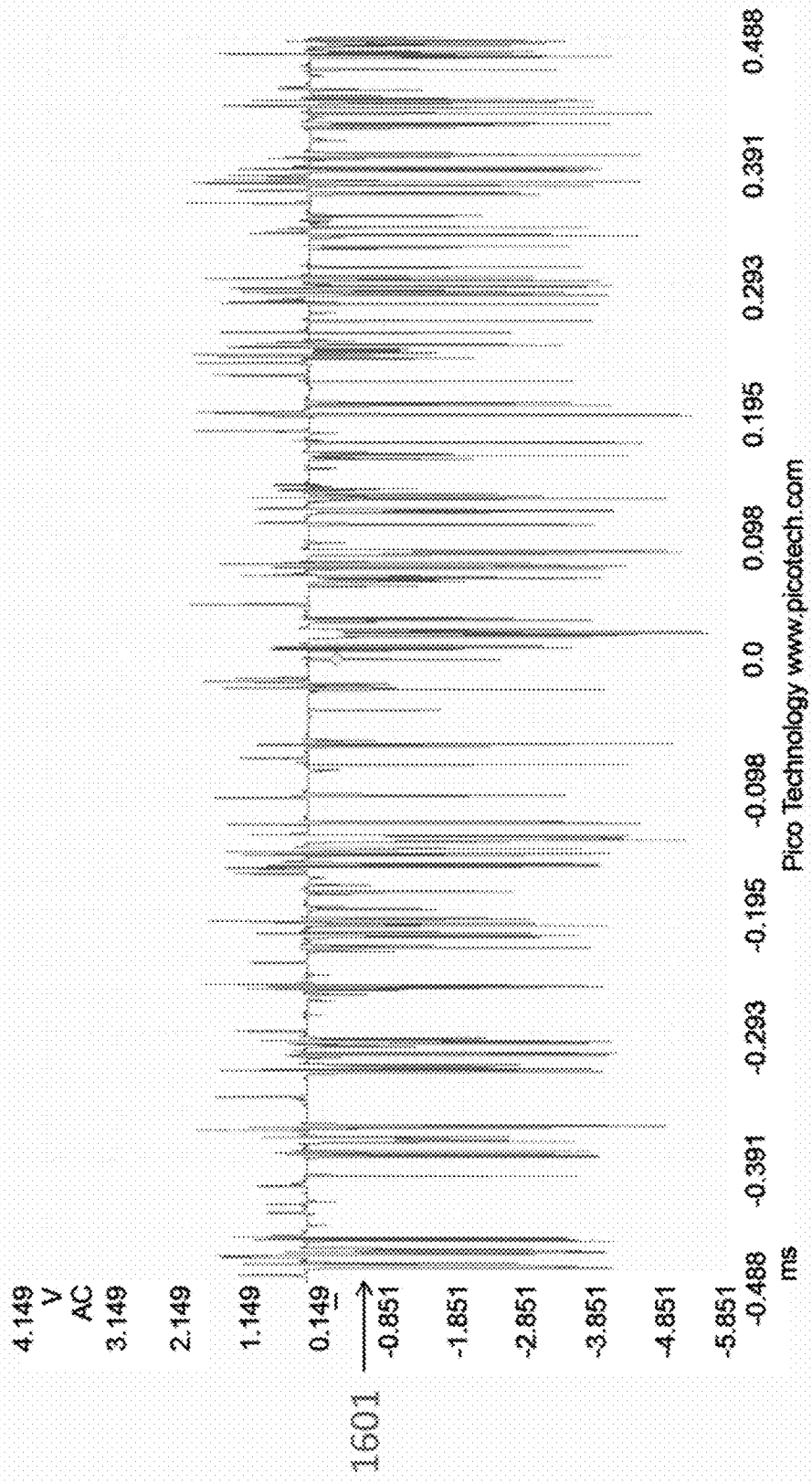
FIG. 16 depicts a representative time domain waveform measured on the human body at an acupuncture point in accordance with an embodiment of the present disclosure.

FIG. 16 depicts an exemplary representative time domain waveform depicting measurements taken on the human body at an acupuncture point. This plot depicts the synaptic action as a function of time. The amplitude is displayed as a relative number. The sensor output is measured in volts and has a proportionality relationship to the synaptic activity. This activity can be measured in the time domain (as shown) or in the frequency domain, depending on what type of analysis is done. The time domain measurement may be used for qualitative measurements and the frequency domain measurement is used for quantitative measurements.

In an embodiment, the sensor is located in a noninvasive handheld contact device. A user interface representing the output of the sensor may be displayed graphically or numerically. The numerical representation shows relative signal levels, which correspond to the maximum signal density (e.g., if there is memory in the sensor, the highest signal within a period of time). In contrast, the graphical display allows for time domain representations (which show variations in detected signals) and frequency domain representations (which show signal diversity as well as relative density as a function of frequency).

In an embodiment, the sensor is configured for synaptic sensing as well as detection of enthalpic processes in both the time domain and the frequency domain. In an embodiment, the sensor provides latencies of microseconds or less.

Correspondence to detected EMG waveforms in structure is encouraging and allows for future investigation. Additional analysis such as 1st and 2nd derivative have been used in signal characterization for various applications.

The presently disclosed detection system may also be employed in a variety of technology areas, exemplary examples of which are listed below.

In embodiments, the detection system is used with radar applications, wherein a particle beam is directed, as a function of time, in a known direction. The detection system is used to sense the return signal.

In embodiments, the detection system is used with various medical, industrial, and communications applications, a directed energy beam is used for selective targeting of various devices and substances. By detecting the particles generated by the beam, information regarding the composition or structure of the target may be gathered.

In embodiments, the detection system is used for the transmission of data. A beam may encode a datastream (e.g., in the beam's modulation). By directing the beam towards an appropriate sensor, the datastream may be detected and demodulated.

In embodiments, the detection system is to carry out complex material inspection by encoding the stimulus so that the detector can differentiate the received signal as a function of time and distance.

In embodiments, the detection system is used for pain detection and evaluation. The metabolic activity at an injury site relative to an adjacent healthy tissue site is indicative of the amount of pain experienced by an individual or animal. For example, this enables a physician to detect both the location and amount of pain experienced by a patient (e.g., based on a detected reaction in a human, animal, or plant) who is unable to communicate. In an embodiment, a pain site may be pinpointed within the millimeter range.

In embodiments, the detection system is used to observe material interaction at the molecular level, allowing for nondestructive qualitative mass spectrography. For example, the system may be used to differentiate between orthogonal molecular samples or to determine the degree of orthogonality (providing a "fingerprint" of the samples to use in comparisons). In an embodiment, the system is used to determine sample uniformity (e.g., whether a sample consists of a single uniform element or composition). In the case of a uniform sample, the spectral display is also uniform from measurement to measurement. Any variation in the spectral display over and above any empirically/statistically determined limits indicates a material nonuniformity.

In an embodiment, the detection system is used for the characterization of nonuniformity in materials such as wood, where the measurement of a knot is desired. With 3-axis measurement capability, a knot's cross-sectional envelope can be determined within the wood sample.

In an embodiment, the system is used with a low power, nonionizing radiation method so as to replace conventional X-ray examination of samples where the thickness and composition of the material is known to have sufficient molecular disparity so as to be able to develop a 2- or 3-dimensional rendition of the sample under test. A fourth dimension, density, can also be included by including the spectral qualities as well as just the envelope magnitude of the measured signal.

In an embodiment, the presence of a sample may be detected by placing sensors 602 on either side of a location where the sample will be placed. In other words, a first sensor 602 is located proximate to the particle generator 302 and a second sensor is located away from the particle generator 302, such that a sample may be placed between the two sensors 602. Here, the medium 604 is air.

FIG. 9 depicts an exemplary embodiment of the peak-to-peak amplitude in dBmV as a function of RF power delivered to the particle generation element in dBm. The process, in terms of dB units, has a monotonic relationship in detected signal in dB, as a function of the increase in RF power.

Figure 10:
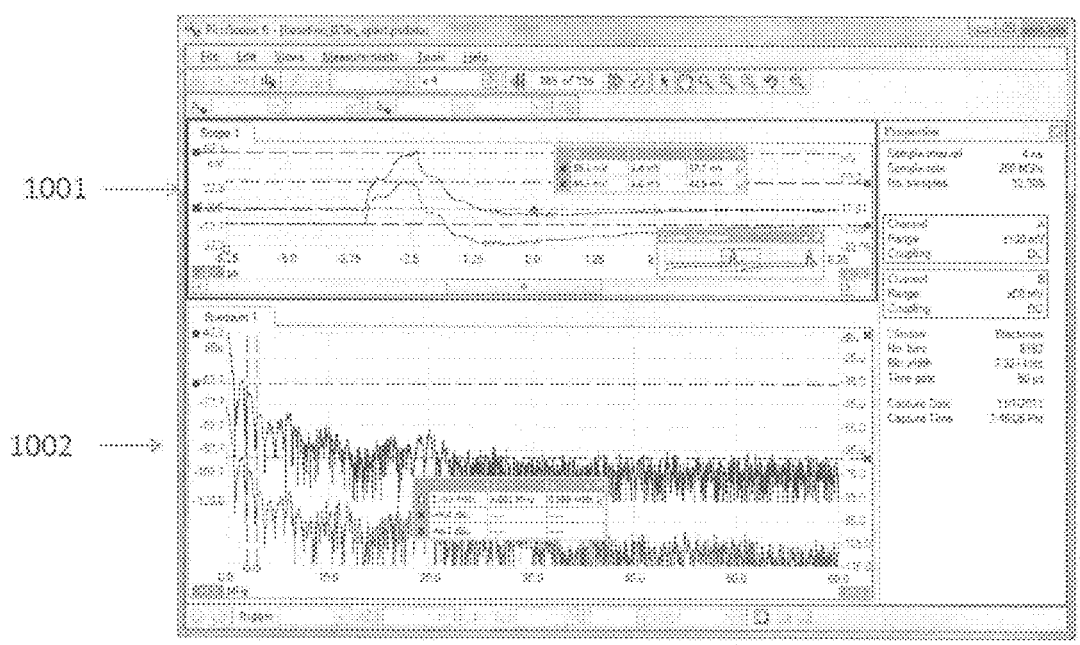
FIG. 10 is a plot depicting both frequency and time domain representations of the output of sensors without a sample present in accordance with an embodiment of the present disclosure.

FIG. 10 depicts time domain representations of the output of sensors 602 without the sample present (e.g., as a setup or baseline measurement). The sensor output is displayed as a trace 1001 (shown as a time domain waveform), where the upper trace is the detected output of the sensor 602 proximate to the particle generator 302 and the lower trace is the detected output of the sensor 602 placed away from the particle generator 302. As shown, without the sample present, the signal is slightly attenuated but the shapes of the waveforms are essentially identical. The lower pair of traces 1002 are frequency domain representations of traces 1001. The two waveforms of the frequency domain traces are also essentially identical.

Figure 11:
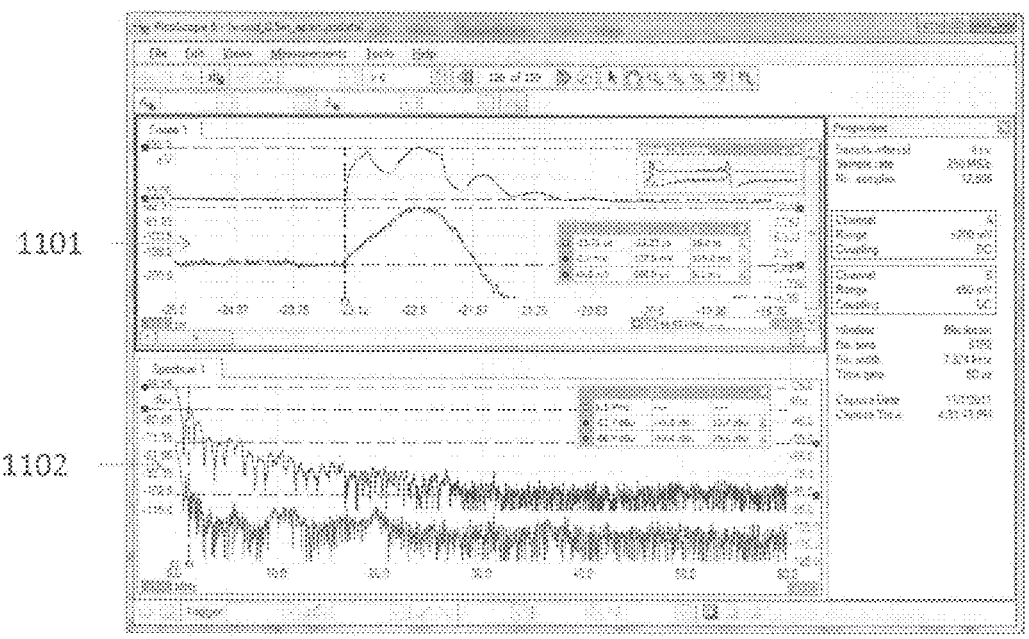
FIG. 11 is a plot depicting both frequency and time domain representations of the output of sensors with a wood sample present in accordance with an embodiment of the present disclosure.

However, when a wood sample is placed between the sensors, the traces change. As shown in FIG. 11, the time domain traces 1101 are no longer similar. There is significant attenuation present in the signal measured from the sensor 602 located on the other side of the sample from the particle generator 302 (i.e., in the particles passing through the sample). Further, the amplitude of the trace generated by the sensor 602 closer to the generator 302 is increased, due to the reflected signal (e.g., the particles reflected off the sample) with the sample present. The spectral information visible in the frequency domain traces 1102 shows that the spectral content differences between the two traces allow for the capability to differentiate whether or not the wood sample is present.

Figure 12:
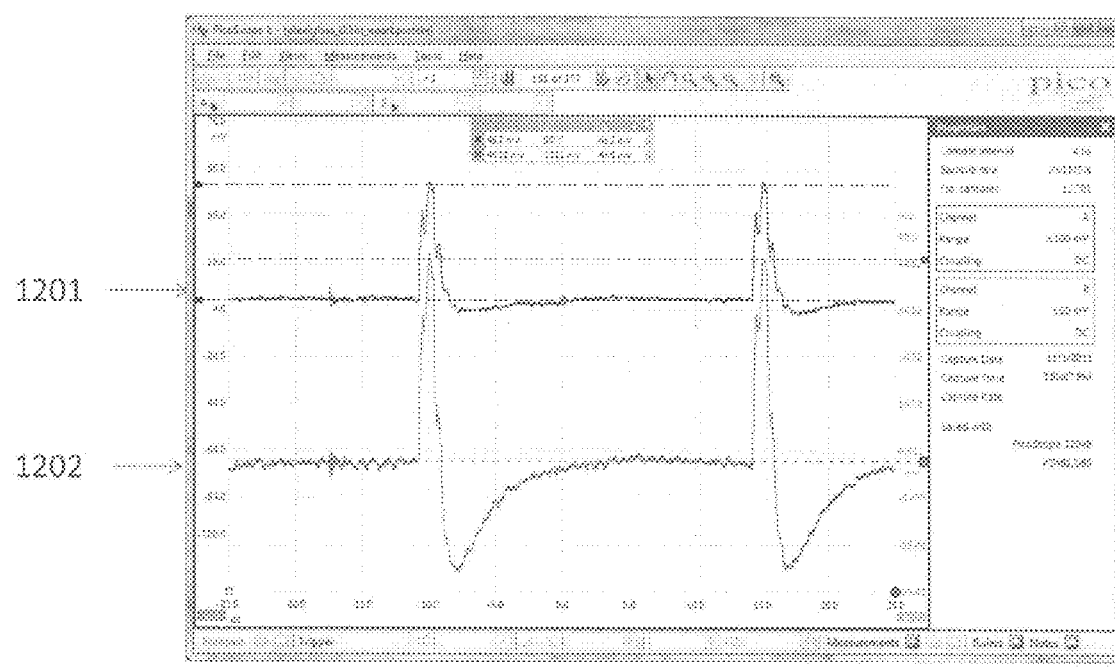
FIG. 12 is a plot depicting time domain representations of the output of sensors with a plexiglass sample present in accordance with an embodiment of the present disclosure.

FIG. 12 depicts the measurements obtained when a plexiglass sample is used. Traces 1201 and 1202 depict time domain measurements. The attenuation of the plexiglass is negligible when compared to the wood case depicted in FIG. 11.

Figure 13:
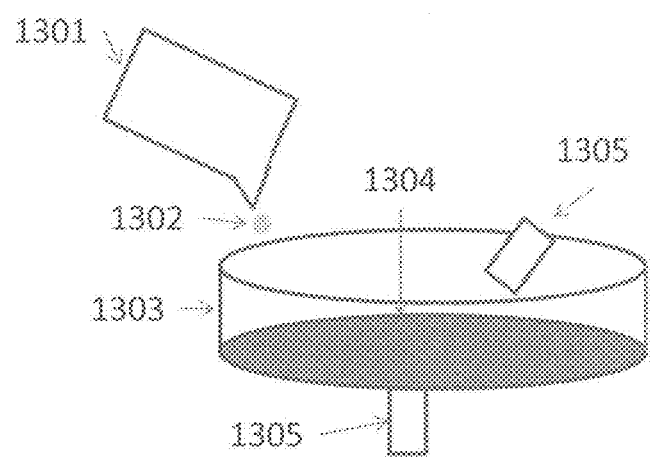
FIG. 13 depicts a method of using a detection system to monitor a reaction in accordance with an embodiment of the present disclosure.

FIG. 13 depicts an exemplary method of using a detection system to monitor a reaction. A vessel 1303 is filled with a substance 1304. A secondary vessel 1301 contains a reagent that interacts (e.g., combines, reacts, neutralizes, etc.) with the substance 1304. As the reagent 1302 is added, the sensor 1305 is used to monitor the interaction as a function of time. The sensor 1305 is located outside of the reaction vessel 1303 so as to minimize (or eliminate) any effect the sensor 1305 may have on the reaction itself. In an embodiment, multiple sensors 1305 are used to measure energy from different locations. Conventionally, reactions are monitored with respect to changes in characteristics such as temperature, color, volume, and texture. Using embodiments of the present disclosure, spectral energy levels during the reaction may be recorded and analyzed. This allows a researcher to observe, either in real time or off-line, how changes in drip rate, temperature, lighting, vibration, gravity, and any other experimental variable impact the observed reaction. By observing the spectral changes as dependent variables, it is possible to determine which components are more or less active and if there is a point in the process where spectral components may dominate or become more passive with regards to the observed process.

Figure 14:
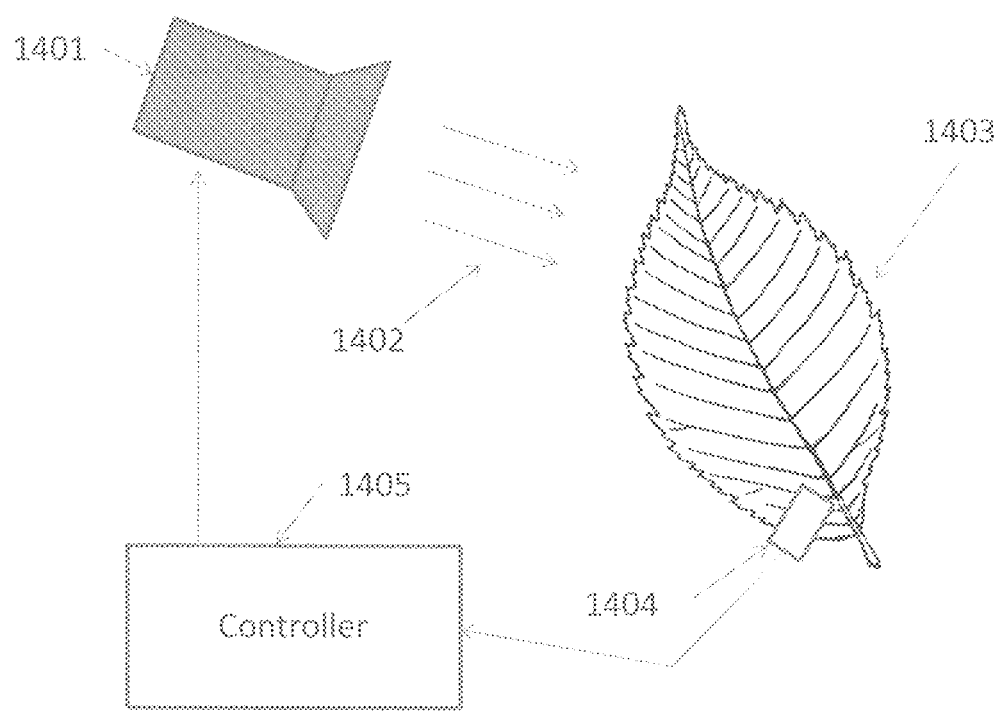
FIG. 14 depicts a method of using a detection system to monitor the effects of stimulus on a leaf in accordance with an embodiment of the present disclosure.

FIG. 14 depicts an exemplary method of using a detection system to monitor the effect of a stimulus 1402 produced by a source 1401 on a leaf 1403 using a sensor 1404. The leaf can be on a plant or separated from the plant. Factors such as the amount of time the leaf has been separated from the plant and the surrounding environmental conditions will impact the resultant measurements captured by the sensor 1404. The composition of the stimulus 1402 may be configured to be very simple or very complex. A simple example would be using only one constituent in the stimulus (e.g., light, sound, air flow, air composition, humidity, rain, fertilizer, etc.). A more complex example would be a combination of one or more of these constituent elements varied over time. For example, a light source could be selective in wavelength, be pulsed, have its constituent wavelength components varied as a function of time or as a dependent variable to the reaction captured by the sensor 1404. Therefore, the composition of the stimulus source 1401 is highly dependent on the stimulus/stimuli it is expected to provide. The sensor 1404 can give a quality value, described as an indicator (which could vary as a function of time), where the indicator could be a number, a light color/intensity, a variable tone, a threshold, a time domain measurement, a frequency domain measurement or any other method chosen to indicate a level, relative or absolute, that is to be measured. In an embodiment, the system utilizes a controller 1405 to manipulate the stimulus. In an embodiment, the controller 1405 optimizes one or more characteristics of the sensor 1404. For example, the controller may adjust the stimulus based on how the leaf/plant reacts, which may be measured either continuously over time or discretely. The point that the sensor monitors may be anywhere on a plant: on the spline of the leaf, along a vein, on a branch, on the trunk, or in the root system. By monitoring the particles emitted or reflected from the plant, information regarding the plant's composition, structure, and activity may be collected.

Figure 15:
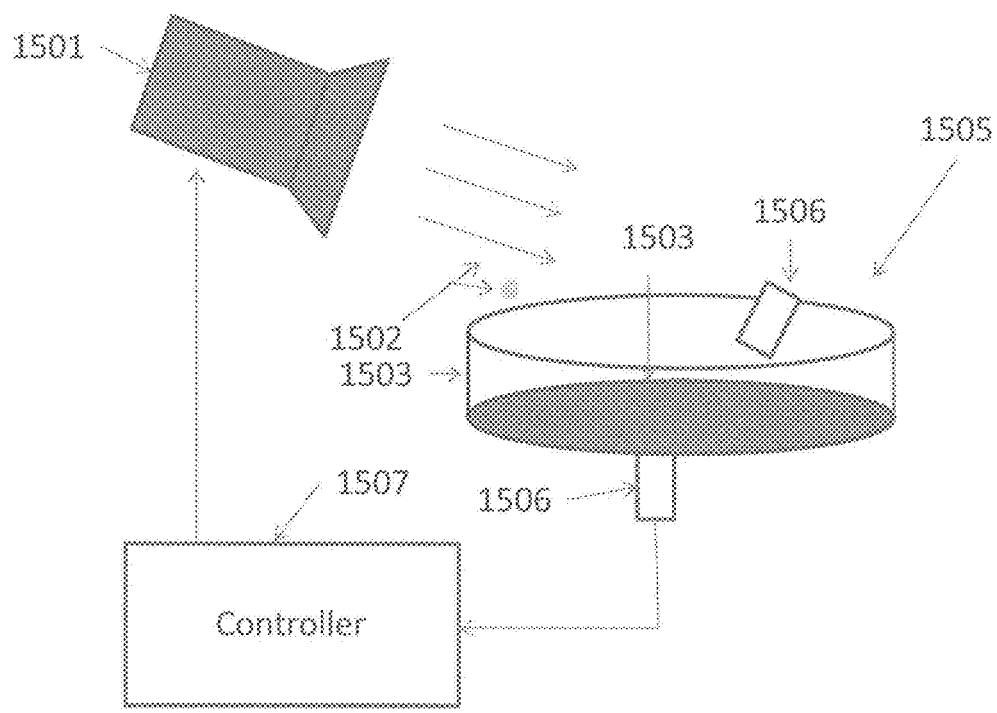
FIG. 15 depicts a method of using a detection system to monitor the activity of a soil sample in accordance with an embodiment of the present disclosure.

FIG. 15 depicts an exemplary method of using a detection system to monitor the activity of a soil sample. The soil sample's viability and activity level may be monitored as a function of the composition of the sample 1503, which will vary over time when being affected by the stimulus 1502. The stimulus 1502 may be monitored and modulated as a function of time and/or the sensor 1506 output.

One of skill in the art will recognize that all the various components identified in this disclosure may be made from any material or combination of materials suitable for the expected structural load and environment, without limitation—metals, composites, engineered plastics, natural or synthetic materials, etc.

Furthermore, while the particular preferred embodiments have been shown and described, it is obvious to those skilled in the art that changes and modifications may be made without departing from the teaching of the disclosure. The matter set forth in the foregoing description and accompanying drawings is offered by way of illustration only and not as limitation. The actual scope of the disclosure is intended to be defined in the following claims when viewed in their proper perspective, based on the related art.

What is claimed is:

1. A sensor apparatus comprising:
a processor coupled to a display;
a power supply with a positive terminal and a negative terminal;
a solid lens member responsive to direct reception of a plurality of modulated secondary emission particles emitted from a target in response to irradiation by one or more corresponding modulated energies by focusing, with the solid lens member, the plurality of modulated secondary emission particles;
at least one semiconductor with a p-type region and an n-type region, wherein the p-type region is coupled to the negative terminal and the n-type region is coupled to the positive terminal via a load, thereby forming a reverse-biased P-N junction in the at least one semiconductor, wherein the reverse-biased P-N junction, in response to direct reception of the focused plurality of modulated secondary emission particles, produces a modulated signal at the load; and
a detector configured to measure the voltage across the load and generate a detected signal;
wherein the processor is coupled to the detector and is configured to:
amplify and filter the detected signal to create a measurement signal; and
provide a display signal to the display that is representative of the measurement signal.

2. The sensor apparatus of claim 1, wherein the at least one semiconductor comprises an NPN transistor, a PNP transistor; a photo transistor, a Darlington transistor, or a reverse-biased photo diode.

3. The sensor apparatus of claim 2, wherein the at least one semiconductor comprises a transistor configured as an emitter follower circuit.

4. The sensor apparatus of claim 1, wherein the at least one semiconductor comprises a plurality of semiconductors.

5. A system for generating excitation signals and receiving excited particles comprising:
a generator configured to emit one or more modulated energies;
a target irradiated by the one or more modulated energies and in response thereto emits a plurality of modulated secondary emission particles;
a receiver comprising a sensor and a beam-focusing element, the beam-focusing element comprising:
a filter which blocks a first portion of the plurality of modulated secondary emission particles and passes a second portion of the plurality of modulated secondary emission particles, and
a solid lens member which focuses the second portion of the plurality of modulated secondary emission particles;
a refraction element which refracts the focused second portion of the plurality of modulated secondary emission particles such that at least a portion of the plurality of refracted and focused modulated secondary emission particles directly impinge on the sensor, wherein the sensor generates an electrical signal in response to the direct impingement of the at least a portion of the plurality of refracted and focused modulated secondary emission particles; and
a controller coupled to the sensor and responsive to the electrical signal by generating another electrical signal representative of the at least a portion of the plurality of refracted and focused modulated secondary emission particles.

6. The system of claim 5, wherein the generator comprises a plurality of generators, the system further comprising a summing network configured to coherently combine the one or more modulated energies emitted by the plurality of generators into a coherent wave front.

7. The system of claim 5, wherein the generator comprises an RF waveguide and the one or more modulated energies comprises modulated RF radiation.

8. The system of claim 5, wherein the generator comprises a laser and the one or more modulated energies comprises modulated light.

9. The system of claim 5, wherein the generator comprises an LED and the plurality of one or more modulated energies comprises modulated light.

10. The system of claim 5, wherein the one or more modulated energies is modulated using amplitude modulation or phase modulation.

11. The system of claim 10, wherein the one or more modulated energies comprises encoded data and the measurement signal is indicative of the encoded data.

12. The system of claim 5, wherein the beam focusing element is configured to separate the plurality of emitted particles based on one or more of composition, energy level, or excitation level.

13. A method for detecting and identifying a characteristic of a sample, the method comprising:
receiving one or more modulated energies at the sample;
receiving directly, with a receiver comprising a sensor, a plurality of corresponding modulated secondary emission particles emitted by the sample in response to the one or more modulated energies, the plurality of modulated secondary emission particles comprising a plurality of desired secondary emission particles and a plurality of undesired secondary emission particles;
filtering the plurality of modulated secondary emission particles such that the plurality of undesired secondary emission particles is prevented from impinging on the sensor and the plurality of desired secondary emission particles is directed towards the sensor;
focusing, with a solid lens member, the plurality of desired emission particles;
responding to direct impingement of the focused plurality of desired secondary emission particles on the sensor by generating, with the receiver, an electrical measurement signal indicative of the optically focused plurality of desired secondary emission particles received by the sensor; and
determining, based on the electrical measurement signal, the characteristic of the sample.

* * * * *